United States Patent
Vaporciyan

(10) Patent No.: US 8,802,884 B2
(45) Date of Patent: Aug. 12, 2014

(54) PROCESS FOR PRODUCING AROMATIC CARBONATES

(71) Applicant: Shell Oil Company, Houston, TX (US)

(72) Inventor: Garo Garbis Vaporciyan, Houston, TX (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 13/706,045

(22) Filed: Dec. 5, 2012

(65) Prior Publication Data

US 2013/0150609 A1   Jun. 13, 2013

Related U.S. Application Data

(60) Provisional application No. 61/567,866, filed on Dec. 7, 2011.

(51) Int. Cl.
*C07C 68/06* (2006.01)
*B01D 3/00* (2006.01)

(52) U.S. Cl.
CPC ............... *C07C 68/06* (2013.01); *B01D 3/009* (2013.01); *C07C 68/065* (2013.01)
USPC ........................................... 558/270

(58) Field of Classification Search
None
See application file for complete search history.

(56) References Cited

U.S. PATENT DOCUMENTS

| 5,334,742 A | 8/1994 | Schön et al. | 558/274 |
| 7,417,161 B2 * | 8/2008 | Woo et al. | 558/270 |
| 2011/0206568 A1 * | 8/2011 | Dux et al. | 422/187 |

FOREIGN PATENT DOCUMENTS

| KR | 20080023533 | 3/2008 |
| WO | 9938823 | 8/1999 |
| WO | WO0100560 | 1/2001 |
| WO | 2011067263 | 6/2011 |

OTHER PUBLICATIONS

PCT International Searching Authority report dated Jun. 4, 2013, Application No. PCT/US2012/067979 filed Dec. 5, 2012.

* cited by examiner

*Primary Examiner* — Brandon Fetterolf
*Assistant Examiner* — Ana Z Muresan

(57) ABSTRACT

This invention provides a method for producing an alkylaryl carbonate comprising:

a) contacting a stream comprising an aromatic hydroxy compound and a stream comprising a dialkylcarbonate in a reactive distillation column containing a bed of heterogeneous transesterification catalyst, the bed having a top and a bottom; and b) withdrawing a product stream comprising the alkylaryl carbonate from the reactive distillation column wherein the aromatic hydroxy compound is fed to the column at a first feed point located above the top of the catalyst bed.

12 Claims, 1 Drawing Sheet

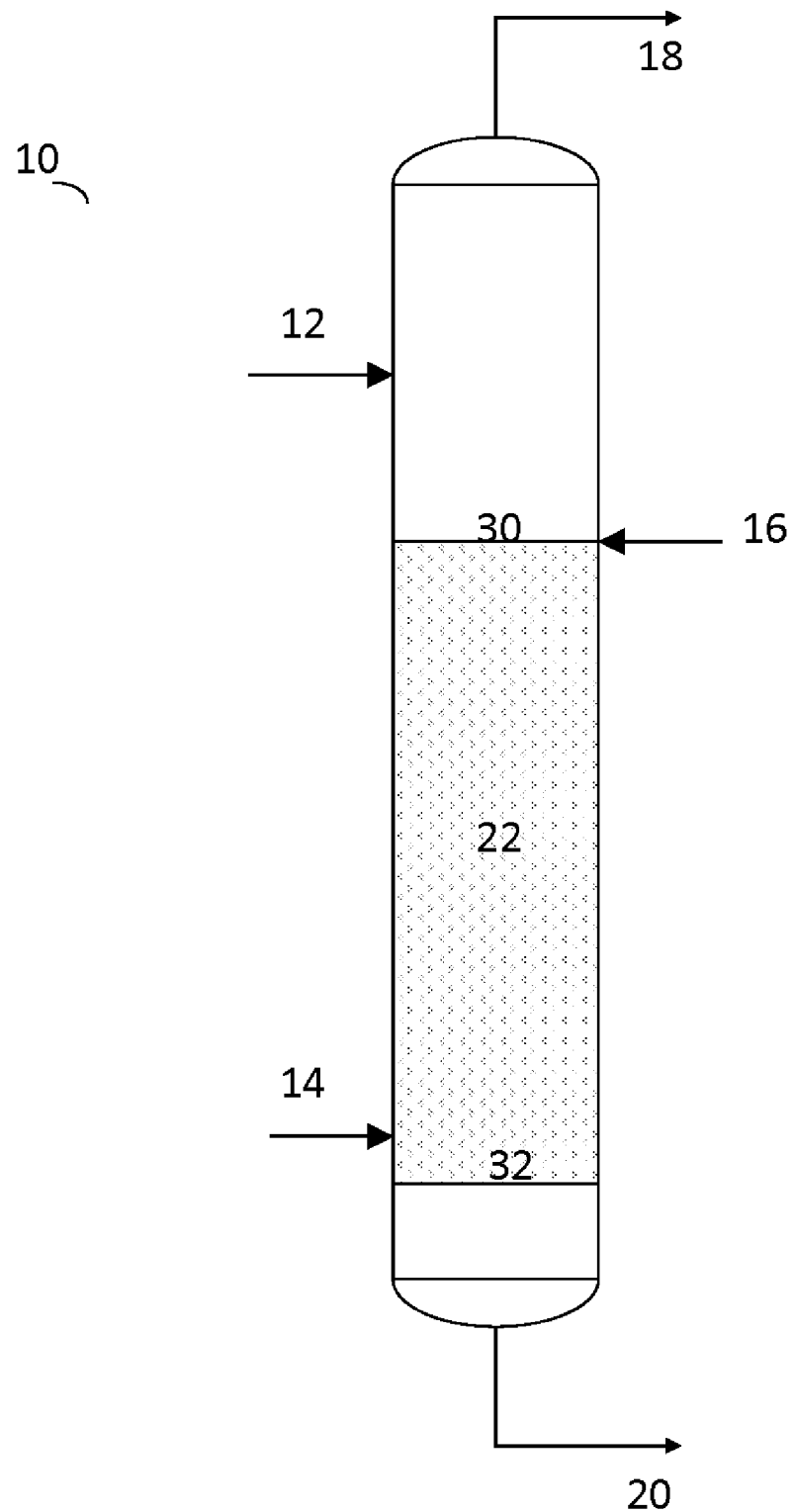

US 8,802,884 B2

PROCESS FOR PRODUCING AROMATIC CARBONATES

CROSS-REFERENCE TO RELATED APPLICATIONS

This application claims the benefit of U.S. Provisional Application No. 61/567,866, filed on Dec. 7, 2011, the entirety of which is herein incorporated by reference.

FIELD OF THE INVENTION

This invention relates to the production of aromatic carbonates.

BACKGROUND OF THE INVENTION

Aromatic carbonates are typically produced by a transesterification reaction between a dialkylcarbonate and an aromatic hydroxy compound. This reaction is typically carried out in the presence of a catalyst to accelerate the transesterification reaction. Aromatic carbonates are useful as raw materials for the production of aromatic polycarbonates that are used as engineering plastics.

U.S. Pat. No. 5,334,742 describes a process for preparing diarylcarbonates by reacting dialkylcarbonates with phenol using conventional transesterification catalysts in a specific mass-coupled and energy-coupled combination of columns. The WO 01/00560 publication describes a process for preparing aromatic carbonates by gas phase reaction or liquid phase reaction of dimethylcarbonate with phenol in the presence of a titanium-silica catalyst followed by the liquid phase reaction of the prepared methylphenylcarbonate in the presence of a titanium-silica catalyst to produce the aromatic carbonates.

SUMMARY OF THE INVENTION

The invention provides a method for producing an aromatic carbonate comprising: contacting a stream comprising an aromatic hydroxy compound and a stream comprising a dialkylcarbonate in a reactive distillation column containing a bed of heterogeneous transesterification catalyst, the bed having a top and a bottom; and withdrawing a product stream comprising the alkylaryl carbonate from the reactive distillation column wherein the aromatic hydroxy compound is fed to the column at a first feed point located above the top of the catalyst bed.

The invention further provides an apparatus for producing an aromatic carbonate comprising: a reactive distillation column having a top outlet and a bottom outlet and at least two inlets; a phenol feed line for transporting phenol which feed line is in fluid communication with one of the inlets; a diethylcarbonate feed line for transporting diethylcarbonate which feed line is in fluid communication with one of the inlets; a top product line for transporting an overhead product that is in fluid communication with the top outlet; a bottom product line for transporting a bottoms product that is in fluid communication with the bottom outlet; a heterogeneous catalyst bed having a top and a bottom that is located in the reactive distillation column wherein the phenol feed line is located above the top of the catalyst bed.

BRIEF DESCRIPTION OF THE DRAWINGS

FIG. 1 depicts an apparatus for the production of aromatic carbonates.

DETAILED DESCRIPTION

The process for producing aromatic carbonates involves the transesterification of dialkylcarbonates and aromatic hydroxy compounds. The aromatic carbonates produced are typically in the form of alkylarylcarbonates, although diarylcarbonates can be formed through a subsequent disproportionation reaction. The aromatic carbonates produced in the reactive distillation column may be alkylarylcarbonates, diarylcarbonates or a mixture thereof.

The dialkylcarbonate is represented by the formula $R^1OCOOR^1$. $R^1$ represents an alkyl group having 1 to 10 carbon atoms, an alicyclic group having 3 to 10 carbon atoms or an aralkyl group having 6 to 10 carbon atoms. Examples of $R^1$ include an alkyl group, such as methyl, ethyl, propyl, allyl, butyl, butenyl, pentyl, hexyl, heptyl, octyl, nonyl, decyl and cyclohexylmethyl and isomers thereof. Further examples of $R^1$ include an alicyclic group, such as cyclopropyl, cyclobutyl, cyclopentyl, cyclohexyl, and cycloheptyl; and an aralkyl group, such as benzyl, phenethyl, phenylpropyl, phenylbutyl, methylbenzyl and isomers thereof.

The alkyl, alicyclic or aralkyl group may be substituted with a substituent such as a lower alkyl group, a lower alkoxy group, a cyano group and a halogen atom.

Examples of the dialkylcarbonate are dimethylcarbonate, diethylcarbonate, dipropylcarbonate, diallylcarbonate, dibutenylcarbonate, dibutylcarbonate, dipentylcarbonate, dihexylcarbonate, diheptylcarbonate, dioctylcarbonate, dinonylcarbonate, didecylcarbonate, dicyclopentylcarbonate, dicyclohexylcarbonate, dicycloheptylcarbonate, dibenzylcarbonate, diphenylcarbonate, di(phenylpropyl)carbonate, di(phenylbutyl)carbonate, di(chlorobenzyl)carbonate, di(methoxybenzyl)carbonate, di(methoxymethyl)carbonate, di(methoxyethyl)carbonate, di(chloroethyl)carbonate, di(cyanoethyl)carbonate and isomers thereof.

A dialkylcarbonate where $R^1$ is an alkyl group having four or less carbon atoms is preferred. The dialkylcarbonate is most preferably diethylcarbonate.

The aromatic hydroxy compound is represented by the formula $Ar^1OH$ where $Ar^1$ represents an aromatic group having 5 to 30 carbon atoms, and the type of compound is not limited as long as the hydroxy group is directly bonded to the aromatic group. Examples of $Ar^1$ include a phenyl group and various alkylphenyl groups, such as, tolyl, xylyl, trimethylphenyl, tetramethylphenyl, ethylphenyl, propylphenyl, butylphenyl, diethylphenyl, methylethylphenyl, pentylphenyl, hexylphenyl, cyclohexylphenyl, and isomers thereof; various alkoxyphenyl groups, such as, methoxyphenyl ethoxyphenyl, butoxyphenyl and isomers thereof; various halogenated phenyl groups, such as fluorophenyl, chlorophenyl, bromophenyl, chloromethylphenyl, dichlorophenyl, and isomers thereof.

Examples of aromatic hydroxy compounds having these $Ar^1$ include phenol; various alkyl phenols, such as cresol, xylenol, trimethylphenol, tetramethylphenol, ethylphenol, propylphenol, butylphenol, diethylphenol, methylethylphenol, methylpropylphenol, dipropylphenol, methylbutylphenol, pentylphenol, hexylphenol and cyclohexylphenol; various alkoxyphenols, such as methoxyphenol and ethoxyphenol; and isomers thereof. An aromatic monohydroxy compound where $Ar^1$ is an aromatic group having from 6 to 10 carbon atoms is preferred and phenol is most preferred.

The transesterification reaction produces an alkylarylcarbonate corresponding to the reactants fed to the reactive distillation column and an alkyl hydroxy compound. In one embodiment, the transesterification reaction is carried out with phenol and diethylcarbonate and the resulting products are ethylphenylcarbonate and ethanol. In another embodiment where the reaction is carried out with phenol and dimethylcarbonate, the resulting transesterification products will be methylphenylcarbonate and methanol.

The transesterification reaction is an equilibrium reaction, and the equilibrium is biased toward the reactants. In addition, the reaction rate is low. To help shift the equilibrium to produce more aromatic carbonates, the reaction is carried out in a reactive distillation column. The reactive distillation column is operated so that the transesterification products are removed in the overhead product stream.

A second equilibrium reaction that occurs in the reactive distillation column is the disproportionation reaction. This reaction occurs when two alkylarylcarbonate molecules disproportionate and form a diarylcarbonate and a dialkylcarbonate. In the embodiment where ethylphenylcarbonate and ethanol are formed by transesterification, the products of the disproportionation reaction would be diphenylcarbonate and diethylcarbonate. In the embodiment where methylphenylcarbonate and methanol are formed, the products of the disproportionation reaction would be diphenylcarbonate and dimethylcarbonate.

The products of the transesterification reaction and/or the disproportionation reaction are removed from the reactive distillation column at one or more outlets and separated and/or recycled to the reactive distillation column or other process units.

The reactive distillation column may contain any internals known to one of ordinary skill in the art to be useful in a reactive distillation column. Examples of suitable columns include plate type columns using a tray, such as a bubble-cap tray, a sieve tray, a valve tray, and a counterflow tray; and packed type columns packed with various packings, such as Raschig ring, a Lessing ring, a Pall ring, a Berl saddle, an Intelox saddle, a Dixon packing, a McMahon packing, a Heli pack, a Sulzer packing and Mellapak.

The heterogeneous catalyst used in this reactive distillation column may be any catalyst known to one of ordinary skill in the art to be useful in accelerating the transesterification reaction. The heterogeneous catalyst may comprise titanium, chromium, tungsten, molybdenum, vanadium, tin, lead, copper, alkali metals, zinc, cadmium, iron, zirconium, Lewis Acid, Lewis Acid-forming compounds or a mixture thereof. The catalyst preferably comprises titanium.

The heterogeneous catalyst may be supported on aluminium oxide, titanium oxide, silicon oxide, active carbon or a mixture thereof. The catalyst is preferably supported on silica. The catalyst is preferably titanium supported on silica.

Further, a homogenous catalyst may be added to the reaction. In one embodiment, the homogenous catalyst may be added to replace metals that are leached from the heterogeneous catalyst. The homogeneous catalyst preferably comprises titanium-ethanolate, titanium-phenolate, or titanium carbonate. The homogeneous catalyst may be fed in a solution of phenol.

The homogeneous catalyst may be added to maintain a specific concentration of metals in the reactive distillation column. The concentration of metals in the column may be monitored by measuring the level of metals in the bottom product stream. The concentration of metals may be in the range of from 10 to 2000 milligram of metal per kilogram of product stream, preferably of from 50 to 250 mg/kg, and more preferably of from 80 to 200 mg/kg.

One of the difficulties encountered in this reaction is that the heterogeneous catalyst is deactivated by contact with water. The aromatic hydroxy compound used as a reactant in this process typically contains water. Even when purified to remove the water a residual amount of water is usually present in the aromatic hydroxy stream. Water may be present in the feed stream comprising the aromatic hydroxy compound in an amount of up to 0.5 wt %, but is preferably only present in an amount of less than 1000 ppmw, more preferably less than 300 ppmw and most preferably less than 150 ppmw. The industrial specification for phenol is 150 ppmw of water and even phenol that meets that specification may result in deactivation of the catalyst.

Some possible methods to remove this water include separating the water in a separate distillation column, and using an adsorbent or absorbent. The use of a dedicated column would result in increased cost and energy use. In addition, it is difficult to find adsorbents or absorbents which can achieve the desired water level but do not leach substances that would have a detrimental effect on the catalyst or process.

The invention provides a method of operating the reactive distillation column to reduce the amount of water that contacts the heterogeneous catalyst without requiring an additional separation of water from the aromatic hydroxy feed that would be expensive or difficult.

The method and the apparatus used to carry out the method will be further described in relation to FIG. 1. It is understood that one of ordinary skill in the art can modify the apparatus and method depicted in FIG. 1 while still carrying out the invention as described and as claimed hereinafter. The Figure does not depict every piece of equipment that would be used in the process including reboilers, condensers, heat exchanges, valves and pumps, but one of ordinary skill in the art could determine where to place these items in the process.

FIG. 1 depicts a reactive distillation column 10 for carrying out a transesterification reaction of a dialkylcarbonate and an aromatic hydroxy compound. A heterogeneous catalyst bed 22 is located inside the reactive distillation column. The catalyst bed has a top 30 and a bottom 32. A catalyst screen or other device for holding the catalyst in place may be located at the top 30 and/or the bottom 32.

The reactive distillation column has an inlet 12 for the aromatic hydroxy compound containing stream that is located above the top 30 of the heterogeneous catalyst bed. The inlet 14 is used for feeding the dialkylcarbonate stream into the column. The inlet 16 is an optional inlet for homogeneous catalyst. In another embodiment, the homogeneous catalyst may be fed into the reactive distillation column through inlet 12 or inlet 14.

The reactive distillation column has an outlet 18 for an overhead product stream that typically comprises a dialkylcarbonate, an alkyl hydroxy compound, and an aromatic hydroxy compound. The column also has an outlet 20 for a bottom product stream that typically comprises an aromatic hydroxy compound, a dialkylcarbonate, an alkylarylcarbonate, diarylcarbonate. Either of the outlets may contain by-products formed during the reaction.

The reactive distillation column is operated under reaction conditions that are conducive to the transesterification reaction. These conditions result in a separation of the water from the stream comprising the aromatic hydroxy compound. The water is removed from the stream before the stream contacts the heterogeneous catalyst, preventing the deactivation of the catalyst.

The column is typically operated at a pressure in the range of from 1 bara to 5 bara, preferably in a range of from 2 to 4 bara. The column is typically operated such that the temperature in the heterogeneous catalyst bed is in a range of from 100° C. to 250° C., preferably in a range of from 150° C. to 230° C. and more preferably in a range of from 170° C. to 210° C.

The column preferably contains some type of internals between the top 30 of the catalyst bed and the inlet 12, for example, trays, packing, Pall rings, Raschig rings or other internals known to one of ordinary skill in the art including those described previously. The internals assist in the separation of the water from the aromatic hydroxy compound.

The vertical distance in a reactive distillation column can be divided into a number of theoretical trays that are needed to effect the desired degree of separation. The distance between the inlet 12 and the top 30 of the catalyst bed is preferably at least one theoretical tray, and preferably at least two theoretical trays.

The effectiveness of the process can be evaluated by determining the amount of water present in the heterogeneous catalyst bed. This can be an absolute measure, and in this case the amount of water in the catalyst bed is preferably less than 250 ppmw calculated against the total amount of aromatic hydroxy compound present in the catalyst bed. The amount of water in the catalyst bed is more preferably less than 150 ppmw, and most preferably less than 100 ppmw.

Another measure of the effectiveness of the process can be a relative measure, and in this case the amount of water present in the aromatic hydroxy compound when it passes into the catalyst bed is less than 80% of the amount of water in the aromatic hydroxy compound before it enters the reactive distillation column. The amount of water present in the aromatic hydroxy compound as it enters the catalyst bed is preferably less than 60% and more preferably less than 40% of the amount of water in the aromatic hydroxy compound before it enters the reactive distillation column The water may be removed through outlet 18 along with the overhead products. The water is typically present in the stream comprising the alkyl hydroxy compound. This stream may be recycled to a unit that produces dialkylcarbonate. The water may be separated from the alkyl hydroxy compound prior to recycling the stream. Alternatively the water may be left in the stream as it does not have a negative effect on the operation of the dialkylcarbonate production unit.

In another embodiment, the reactive distillation column contains an additional catalyst bed that is located above the first catalyst bed. This catalyst bed contains a catalyst that accelerates the reaction between water and the dialkylcarbonate present in the column to produce carbon dioxide and an alkyl hydroxy compound that are already present in the column and not harmful to the transesterification catalyst.

What is claimed is:

1. A method for producing an alkylaryl carbonate comprising:
    a) contacting a stream comprising an aromatic hydroxy compound and water, and a stream comprising a dialkylcarbonate in a reactive distillation column containing a bed of heterogeneous transesterification catalyst, the bed having a top and a bottom; and
    b) withdrawing a product stream comprising the alkylaryl carbonate from the reactive distillation column
        wherein the aromatic hydroxy compound is fed to the column at a first feed point located at least one theoretical tray above the top of the catalyst bed; wherein the aromatic hydroxy compound has a water content of less than 0.5 wt % when it first contacts the top of the heterogeneous transesterification catalyst bed.

2. A method as claimed in claim 1 where the reactive distillation column contains an item selected from the group consisting of trays and packing between the top of the catalyst bed and the first feed point.

3. A method as claimed in claim 1 where the reactive distillation column contains a second catalyst bed between the top of the catalyst bed and the first feed point.

4. A method as claimed in claim 3 wherein the second catalyst accelerates the reaction of water with dialkylcarbonate.

5. A method as claimed in claim 1 further comprising feeding a homogeneous transesterification catalyst to the reactive distillation column.

6. A method as claimed in claim 5 wherein the homogeneous transesterification catalyst is fed to the column at a point below the first feed point.

7. A method as claimed in claim 1 wherein the aromatic hydroxy compound is phenol.

8. A method as claimed in claim 1 wherein the dialkylcarbonate is selected from the group consisting of dimethyl carbonate, diethyl carbonate and mixtures thereof.

9. A method as claimed in claim 1 wherein the dialkylcarbonate is fed to the reactive distillation column at a point below the top of the catalyst bed.

10. A method as claimed in claim 1 wherein the dialkylcarbonate is fed to the reactive distillation column at a point below the bottom of the catalyst bed.

11. A method as claimed in claim 1 wherein the heterogeneous catalyst comprises titanium.

12. A method as claimed in claim 1 wherein the aromatic hydroxy compound has a water content of less than 500 ppmw when it first contacts the top of the heterogeneous transesterification catalyst bed.

* * * * *